United States Patent
Wang

(10) Patent No.: US 10,339,652 B2
(45) Date of Patent: Jul. 2, 2019

(54) IMAGE RECONSTRUCTION

(71) Applicant: Shenyang Neusoft Medical Systems Co., Ltd., Shenyang (CN)

(72) Inventor: Hongbo Wang, Shenyang (CN)

(73) Assignee: Shenyang Neusoft Medical Systems Co., Ltd., Shenyang (CN)

(*) Notice: Subject to any disclaimer, the term of this patent is extended or adjusted under 35 U.S.C. 154(b) by 181 days.

(21) Appl. No.: 15/612,300

(22) Filed: Jun. 2, 2017

(65) Prior Publication Data

US 2017/0352155 A1 Dec. 7, 2017

(30) Foreign Application Priority Data

Jun. 2, 2016 (CN) .......................... 2016 1 0389016

(51) Int. Cl.
| | | |
|---|---|---|
| *G06K 9/00* | (2006.01) | |
| *G06T 7/00* | (2017.01) | |
| *A61B 6/00* | (2006.01) | |
| *G06T 11/00* | (2006.01) | |

(52) U.S. Cl.
CPC ............ *G06T 7/0012* (2013.01); *A61B 6/488* (2013.01); *A61B 6/5205* (2013.01); *A61B 6/545* (2013.01); *G06T 11/003* (2013.01)

(58) Field of Classification Search
CPC ....... A61B 6/488; A61B 6/5205; A61B 6/545; G06T 7/0012
See application file for complete search history.

(56) References Cited

U.S. PATENT DOCUMENTS

| | | | |
|---|---|---|---|
| 9,848,846 B2* | 12/2017 | Zhou | A61B 6/032 |
| 9,974,495 B2* | 5/2018 | Ishii | A61B 6/035 |
| 2003/0043956 A1 | 3/2003 | Cherek et al. | |
| 2013/0101079 A1 | 4/2013 | Hough et al. | |

FOREIGN PATENT DOCUMENTS

| | | |
|---|---|---|
| CN | 102232835 A | 11/2011 |
| CN | 103494613 A | 1/2014 |
| CN | 103892859 A | 7/2014 |
| CN | 104203104 A | 12/2014 |
| CN | 104545973 A | 4/2015 |
| JP | 2012040284 A | 3/2012 |

OTHER PUBLICATIONS

State Intellectual Property Office of the People's Republic of China, Office Action and Search Report Issued in Application No. 201610389016.5, dated May 4, 2018, 7 pages, and an English summary of the Office Action.

* cited by examiner

*Primary Examiner* — Tom Y Lu
(74) *Attorney, Agent, or Firm* — Fish & Richardson P.C.

(57) ABSTRACT

Methods, systems, and computer-readable storage mediums for image reconstruction are provided. An example of the methods includes obtaining an auxiliary scanning condition, performing an auxiliary scanning using the auxiliary scanning condition to generate an auxiliary image, and in response to a determination to perform a primary scanning based on the auxiliary image, determining a first primary scanning condition using the auxiliary scanning condition and performing the primary scanning using the first primary scanning condition to generate a primary image.

19 Claims, 5 Drawing Sheets

IMAGE RECONSTRUCTION

CROSS REFERENCE TO RELATED APPLICATIONS

This application claims priority under 35 U.S.C. § 119 to Chinese Patent Application No. 201610389016.5 which was filed on Jun. 2, 2016, the entire content of which is incorporated herein by reference.

TECHNICAL FIELD

The present disclosure relates to medical imaging diagnostics, and more particularly to image reconstruction.

BACKGROUND

For medical devices that collect medical images, for example, Computed Tomography (CT) devices, in order to collect images that may be used for diagnostics (referred to herein as primary images for convenience of description), in a conventional method, a pilot image scanning is performed on an object to obtain pilot images, and a scanning range and one or more scanning parameters are determined using the pilot images. After the pilot image scanning is completed, the object is scanned based on a scanning condition set by an operator to obtain the primary images. For convenience of description, the scanning process in which the primary image is obtained is referred to as a primary scanning, and the corresponding scanning condition is referred to as a primary scanning condition.

The operator can set the primary scanning condition according to his/her own experience, but the primary scanning condition set by the operator may not be suitable due to subjective or objective factors. When the medical devices use the primary scanning condition to perform the primary scanning on the object, the obtained primary image may not meet requirements. For example, the image quality of the primary image cannot meet the diagnostic requirement so that the object cannot be diagnosed using the currently obtained primary image. In this case, the operator may have to re-set the primary scanning condition, and the medical devices then have to perform the primary scanning on the object under the new primary scanning condition, which causes the object to suffer from additional scanning radiation.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the object during the CT scanning process.

SUMMARY

The present disclosure provides methods, systems, and computer-readable mediums for image reconstruction, which can avoid repeatedly performing primary scanning on an object, thus avoid the object suffering from additional scanning radiation.

In general, one innovative aspect of the subject matter described in the present disclosure can be embodied in methods that include the actions of obtaining an auxiliary scanning condition; performing an auxiliary scanning on an object using the auxiliary scanning condition to generate an auxiliary image; and in response to a determination to perform a primary scanning based on the auxiliary image, determining a first primary scanning condition based on the auxiliary scanning condition and performing the primary scanning on the object using the first primary scanning condition to generate a primary image.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, performing an auxiliary scanning can include generating a plurality of auxiliary images, and performing a primary scanning can include generating a plurality of primary images, and a number of the plurality of auxiliary images can be smaller than a number of the plurality of the primary images. A scanning dose for the auxiliary scanning can be smaller than a scanning dose for the primary scanning.

In some implementations, obtaining an auxiliary scanning condition includes: determining an event indicating a need for an auxiliary scanning occurs; determining an auxiliary scanning scheme corresponding to the event based on a pre-configured relationship between the event and the auxiliary scanning scheme; and obtaining the auxiliary scanning condition corresponding to the event using the auxiliary scanning scheme.

In some examples, determining an event indicating a need for an auxiliary scanning occurs includes: performing a pilot image scanning to generate a pilot image; determining a second primary scanning condition; and determining the event indicating a need for an auxiliary scanning occurs using at least one of the pilot image or the second primary scanning condition.

In some examples, determining an event indicating a need for an auxiliary scanning occurs comprises at least one of: determining that the object contains a metal fixture using the pilot image and the event is a metal fixture event, determining that a scanning field of view of the object is abnormal using the pilot image and the event is a scanning field of view abnormality event, determining that a key region image of the object needs to be viewed using the second primary scanning condition and the event is a key region image viewing event, determining that a scanning dose in the second primary scanning condition is less than a preset first dose or greater than a preset second dose and the event is a primary scanning condition abnormality event, the preset second dose being greater than the preset first dose, or determining that a current curve is predicted by using the pilot image to be abnormal and the event is a variable current abnormality event, wherein the current curve indicates a relationship between scanning angles and bulb tube currents, and the primary scanning is performed at each of the scanning angles based on a corresponding bulb tube current that is determined based on the current curve.

Determining that a current curve is predicted by using the pilot image to be abnormal can include: determining, based on the pilot image, that a difference between attenuation values of adjacent groups of pixel points is greater than a preset threshold, where each of the adjacent groups includes a plurality of adjacent pixel points along a first direction of the pilot image, and an attenuation value of each pixel point along the first direction is a sum of attenuation values of corresponding pixel points along a second direction of the pilot image perpendicular to the first direction, and the attenuation values are associated with the bulb tube currents and the scanning angles.

In some examples, obtaining the auxiliary scanning condition corresponding to the event using the auxiliary scanning scheme includes: analyzing a modifying strategy from the auxiliary scanning scheme; and modifying the second primary scanning condition using the modifying strategy to obtain the auxiliary scanning condition corresponding to the event. The second primary scanning condition can include one or more of a scanning range, a scanning dose, a pitch, a slice combination, a focus mode, a rotational velocity, and a scanning bed position, and the scanning dose can include at least one of a bulb tube current and a bulb tube voltage, and the slice combination can include a number of scanning slices and a thickness of the scanning slices.

In some examples, the modifying strategy includes at least one of: a strategy of modifying the scanning range to a metal fixture range and a strategy of modifying the scanning dose to a preset scanning dose range, when the event is a metal fixture event, a strategy of modifying the scanning range to a supervision-field range and a strategy of moving the scanning bed position to a set position, when the event is a scanning field of view abnormality event, at least one of a strategy of reducing the number of scanning slices in the slice combination and a strategy of reducing the thickness of the scanning slices in the slice combination, when the event is a key region image viewing event, a strategy of modifying the scanning dose to a preset scanning dose range, when the event is a primary scanning condition abnormality event, or a strategy of reducing the scanning dose and a strategy of increasing the pitch, when the event is the variable current abnormality event.

In some implementations, the determination to perform the primary scanning based on the auxiliary image includes one of: a determination that an image quality of the auxiliary image meets a diagnostic requirement for the object, or a determination that an image quality of the auxiliary image cannot meet the diagnostic requirement and that an image quality of a second auxiliary image with a modified auxiliary scanning condition meets the diagnostic requirement.

The method can further include: providing the auxiliary image to an operator; receiving an analyzed result of the auxiliary image from the operator; and determining to perform the primary scanning based on the received analyzed result by determining one of: the image quality of the auxiliary image meets a diagnostic requirement for the object, and the image quality of the auxiliary image does not meet the diagnostic requirement, and an image quality of a second auxiliary image with a modified auxiliary scanning meets the diagnostic requirement.

The method can further include one of: in response to receiving a command to perform the primary scanning, determining to perform the primary scanning based on the auxiliary image, and in response to receiving a command not to perform the primary scanning, re-obtaining the auxiliary scanning condition based on the auxiliary image and performing a second auxiliary scanning using the re-obtained auxiliary scanning condition.

In some examples, determining a first primary scanning condition based on the auxiliary scanning condition includes: analyzing the auxiliary image based on a diagnostics requirement; and modifying, based on a result of the analyzing, the auxiliary scanning condition to be the first primary scanning condition. In some examples, determining a first primary scanning condition based on the auxiliary scanning condition includes: determining that the auxiliary scanning condition is not modified by an operator; and determining the auxiliary scanning condition to be the first primary scanning condition. In some examples, determining a first primary scanning condition based on the auxiliary scanning condition includes: determining that the auxiliary scanning condition is modified by an operator; and determining the modified auxiliary scanning condition to be the first primary scanning condition.

In some implementations, the method further includes: determining, based on the auxiliary image generated at a first scanning position, first attenuation paths at a plurality of respective scanning angles, each of the first attenuation paths corresponding to a respective bulb tube current; generating a first current curve to indicate a relationship between the respective scanning angles and the respective bulb tube currents; and performing the primary scanning at the first scanning position using the determined first current curve.

In some implementations, the method further includes: estimating a second attenuation path at each of the plurality of scanning angles at a second scanning position using a first attenuation path of the first current curve corresponding to the scanning angle, determining a second current curve based on the estimated second attenuation paths; and performing a second primary scanning at the second scanning position using the determined second current curve.

The terminology used in the present disclosure is for the purpose of describing particular examples only, and is not intended to be limiting of the present disclosure. The singular forms such as "a", "said", and "the" used in the present disclosure and the claims are also intended to include the plurals, unless the context clearly indicates otherwise. It is also to be understood that the term "and/or" as used herein refers to any or all possible combinations that include one or more associated listed items.

It is to be understood that although different information may be described using the terms such as first, second, third, etc. in the present disclosure, these information should not be limited to these terms. These terms are used only to distinguish the same type of information from each other. For example, the first information may also be referred to as the second information without departing from the scope of the present disclosure, and similarly, the second information may also be referred to as the first information. Depending on the context, in addition, the used word "if" may be interpreted as "when" or "as" or "determining in response to".

The details of one or more embodiments of the subject matter described in the present disclosure are set forth in the accompanying drawings and description below. Other features, aspects, and advantages of the subject matter will become apparent from the description, the drawings, and the claims.

DETAILED DESCRIPTION

Figure 1:
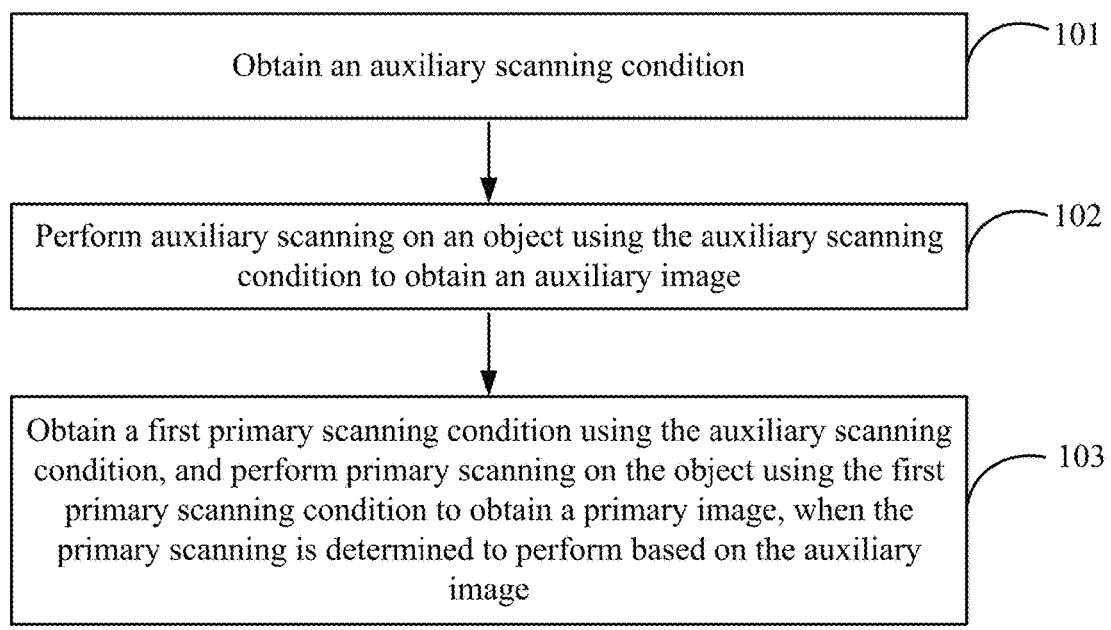
FIG. 1 is a flowchart of a process of image reconstruction in accordance with one or more examples of the present disclosure.

FIG. 1 is a flowchart of a process of image reconstruction in accordance with one or more examples of the present disclosure. The process of image reconstruction may be applied to a medical device, for example, a CT device, a Positron Emission Tomography-Computed Tomography (PET-CT) device, a Digital Radiography (DR) device, a MRI (Magnetic Resonance Imaging System) device, or the like.

Figure 2:
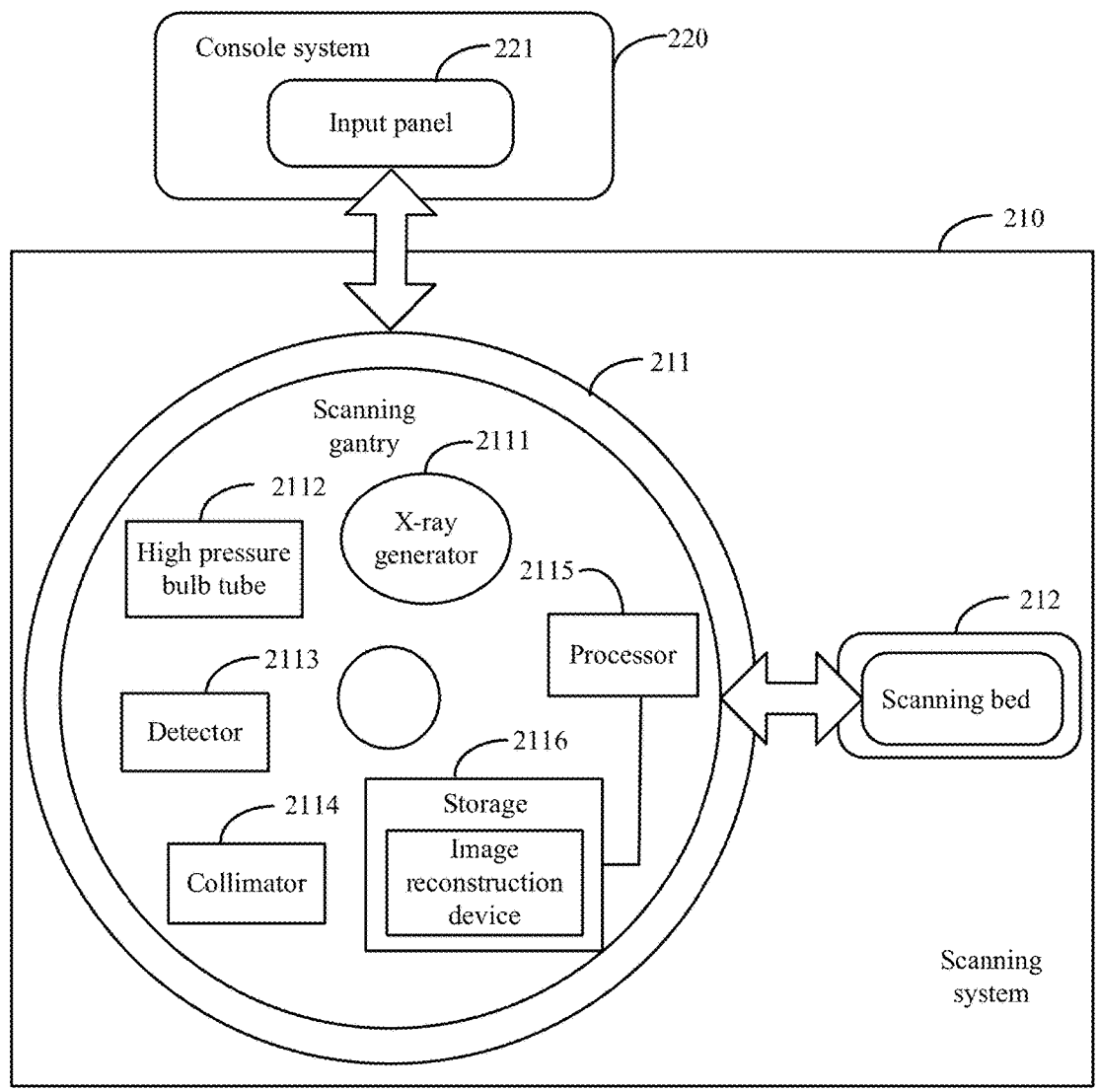
FIG. 2 is a hardware structure diagram of a medical device in accordance with one or more examples of the present disclosure.

FIG. 2 is a hardware structure diagram of a medical device in accordance with one or more examples of the present disclosure. The medical device includes a scanning system 210 and a console 220. The scanning system 210 may include a scanning gantry 211 and a scanning bed 212. The scanning gantry 211 is an important component of the medical device on which an X-ray generator 2111, a high-pressure bulb tube 2112, a detector 2113, a collimator 2114, a processor 2115 and a storage 2116 are positioned. The scanning bed 212 is a tool for cooperating with the scanning gantry 211 to complete a scanning task and is used for supporting an object. The console 220 may include an input panel 221 for an operator inputting a scanning condition through the input panel 221. The image reconstruction device in the storage 2116 may include a logic device, and the processor 2115 may read computer program instructions corresponding to the medical device from the storage 2116 to a memory for operation to realize a process of image reconstruction, e.g., the process of FIG. 1. A computer-readable storage medium may include a storage 2116 and the memory.

In an example of the present disclosure, the scanning condition may include, but is not limited to, one or more of a scanning range, a scanning dose, a pitch, a slice combination, a focus mode, a rotational velocity, a scanning bed position, and any combination thereof. The scanning dose refers to at least one of intensities of a bulb tube current and a bulb tube voltage during an X-ray generator emitting X-rays. A unit of the bulb tube current is milliampere, and a unit of the bulb tube voltage is kilovolt. The slice combination refers to the number of scanning slices*the thickness of the scanning slices. For example, the slice combination can be 16 slices*0.625 mm, which denotes that total 16 slices are scanned and the scanning thickness of each slice is 0.625 mm.

In subsequent processes, a first primary scanning condition, a second primary scanning condition and an auxiliary scanning condition are involved, and each of the first primary scanning condition, the second primary scanning condition, and the auxiliary scanning condition may include a scanning range, a scanning dose (a bulb tube current and/or a bulb tube voltage), a pitch, a slice combination, a focus mode, a rotational velocity, a scanning bed position, and the like. The first primary scanning condition, the second primary scanning condition, and the auxiliary scanning condition are only for convenience of distinguishing. The examples of the scanning conditions in different processes may only differ in the names of the scanning conditions.

Referring to FIG. 1, in step 101, an auxiliary scanning condition is obtained.

In some examples, whether an event needing an auxiliary scanning has taken place (or occurs) is determined. That is, the event indicates a need for the auxiliary scanning or a need for performing the auxiliary scanning. If the event occurs, an auxiliary scanning scheme corresponding to the event can be obtained according to a corresponding relationship between a pre-configured event (corresponding to the event) and the auxiliary scanning scheme (or a pre-configured relationship between the event and the auxiliary scanning scheme), and an auxiliary scanning condition corresponding to the event is obtained according to the auxiliary scanning scheme. In some examples, the process of determining whether an event needing an auxiliary scanning has taken place may specifically include performing a pilot image scanning on an object to obtain a pilot image and obtaining a second primary scanning condition. Whether the event needing an auxiliary scanning has taken place can be determined according to at least one of the pilot image and the second primary scanning condition.

Prior to performing a primary scanning, the medical device may place the object in different positions based on clinical manifestations and individual characteristics of the object. After the object is placed in a position, the pilot image scanning may be performed on the object to obtain a pilot image, that is, a positioning film. The pilot image scanning can be performed according to a preset scanning condition in the medical device. Based on the pilot image, the scanning range and the scanning parameter of the object are determined for an operator to perform further scanning diagnosis and processing.

In some examples, an operator may set the second primary scanning condition according to experience, and the medical device may obtain the second primary scanning condition input by the operator. In some examples, the second primary scanning condition may be pre-configured in the medical device, and the medical device may obtain the pre-configured second primary scanning condition, e.g., without performing the pilot image scanning. In some examples, the second primary scanning condition is set based on the pilot image and/or the preset scanning condition, e.g., automatically by the medical device or by an operator. Of course, there may be other manners of obtaining the second primary scanning condition, which are not described in detail in the present disclosure.

In some examples, the process of determining whether an event needing an auxiliary scanning has taken place includes, but not limited to, at least one of conditions as follows: determining that an event needing an auxiliary scanning has taken place and the event is a metal fixture event if a metal fixture in an object is determined using the pilot image; or, determining that an event needing an auxiliary scanning has taken place and the event is a scanning field of view abnormality event if abnormal scanning field of view of an object is determined using the pilot image; or, determining that an event needing an auxiliary scanning has taken place and the event is a key region image viewing event if the key region image of an object is determined to be viewed using the second primary scanning condition; or, determining that an event needing an auxiliary scanning has taken place and the event is a primary scanning condition abnormality event if scanning dose in the second primary scanning condition is less than a preset first dose or greater than a preset second dose which is greater than the preset first dose; or, determining that an event needing an auxiliary scanning has taken place and the event is a variable current abnormality event if an abnormal current curve is predicted using the pilot image, wherein the current curve is expressed as a corresponding relationship between a scanning angle and a bulb tube current, and in the primary scanning process, the bulb tube current corresponding to the scanning angle may be obtained from the current curve for each scanning angle, and the primary scanning is performed at the scanning angle based on the bulb tube current.

In some examples, the process of performing an auxiliary scanning may be trigger by the operator, that is, when a command for performing the auxiliary scanning input by the operator is received, an event needing an auxiliary scanning is directly determined.

If the event needing an auxiliary scanning has taken place, the auxiliary scanning scheme corresponding to the event may be obtained according to the corresponding relationship between the pre-configured event (corresponding to the event) and the auxiliary scanning scheme. In some examples, a medical device may be pre-configured with the corresponding relationship between an event and an auxiliary scanning scheme, such as a corresponding relationship between the metal fixture event and an auxiliary scanning scheme R1, a corresponding relationship between the scanning field of view abnormality event and an auxiliary scanning scheme R2, and the like. Based on the corresponding relationship between the event and the auxiliary scanning scheme, the corresponding auxiliary scanning scheme may be obtained after determining the event needing an auxiliary scanning that takes place currently and what the event is.

Table 1 is an example of pre-configured events and corresponding auxiliary scanning schemes. For example, when the event needing an auxiliary scanning that takes place currently is determined to be the metal fixture event, the auxiliary scanning scheme is modifying the scanning range to a metal fixture range and modifying the scanning dose to a preset scanning dose range.

TABLE 1

Events and corresponding auxiliary scanning schemes

| Event needing auxiliary scanning | Auxiliary scanning scheme |
| --- | --- |
| Metal fixture event | Modifying a scanning range to a metal fixture range and modifying a scanning dose to a preset scanning dose interval |
| Scanning field of view abnormality event | Modifying a scanning range to supervision field range and moving a scanning bed position to a set position |
| Key region image viewing event | Reducing the number of scanning slices in slice combination and/or reducing the thickness of the scanning slices in the slice combination |
| Primary scanning condition abnormality event | Modifying a scanning dose to a preset scanning dose range |
| Variable current abnormality event | Reducing a scanning dose and increasing a pitch |

After obtaining the auxiliary scanning scheme corresponding to the event needing an auxiliary scanning, the auxiliary scanning condition corresponding to the event may be obtained using the obtained auxiliary scanning scheme. The auxiliary scanning scheme gives modification strategies of a scanning condition, e.g., for modifying a second primary scanning condition. Based on this, the process of obtaining the auxiliary scanning condition corresponding to the event using the auxiliary scanning scheme may include analyzing a modifying strategy of the scanning condition from the auxiliary scanning scheme, and modifying a second primary scanning condition using the modifying strategy to obtain a modified second primary scanning condition, which can be considered as the auxiliary scanning condition corresponding to the event.

For the process of modifying the second primary scanning condition, in some examples, the medical device may directly modify the second primary scanning condition to obtain the auxiliary scanning condition. In some examples, the medical device may also provide the auxiliary scanning scheme to an operator and the operator may modify the second primary scanning condition using the auxiliary scanning scheme. In this way, the medical device can obtain the auxiliary scanning condition.

For the process that a medical device modifies the second primary scanning condition using the modifying strategy of the scanning condition to obtain the auxiliary scanning condition corresponding to the event may specifically include, but is not limited to, at least one of the following cases:

Case 1: if the event is a metal fixture event, the modifying strategy of the scanning condition may include a strategy of modifying the scanning range to a metal fixture range and a strategy of modifying the scanning dose to a preset scanning dose range. Based on the strategy of modifying the scanning range to the metal fixture range, the medical device may modify the scanning range in the second primary scanning condition to the metal fixture range, for example, modifying a range A to a range B. Based on the strategy of modifying the scanning dose to the preset scanning dose range, the medical device may modify the scanning dose in the second primary scanning condition to the preset scanning dose range, for example, modifying a bulb tube current A that is not in the preset scanning dose range to a bulb tube current B in the preset scanning dose range.

The preset scanning dose range may be set according to actual experience. For example, it may be related to material, volume, or other factors of the metal fixture. For example, when the material of the metal fixture is K1 and the volume is v1, the preset scanning dose range is set as L1;

when the material of the metal fixture is K1 and the volume is v2, the preset scanning dose interval is set as L2; and when the material of the metal fixture is K2 and the volume is v1, the preset scanning dose interval is set as L3. Accordingly, when the metal fixture event takes place or occurs, the material and the volume of the metal fixture in the object may be obtained to determine a corresponding preset scanning dose range, and the subsequent processing is then performed based on the determined corresponding preset scanning dose range.

Case 2: when the event is the scanning field of view abnormality event, the modifying strategy of the scanning condition may include a strategy of modifying the scanning range to a supervision-field range and a strategy of moving the scanning bed position to a set position. Based on the strategy of modifying the scanning range to the supervision-field range, the medical device may modify the scanning range in the second primary scanning condition to the supervision-field range, for example, modifying a range A to a range C. Based on the strategy of moving the scanning bed position to the set position, the medical device may modify the scanning bed position in the second primary scanning condition to the set position, for example, modifying the scanning bed position to a position A.

Case 3: when the event is the key region image viewing event, the modifying strategy of the scanning condition may include a strategy of reducing the number of scanning slices in the slice combination and a strategy of reducing the thickness of the scanning slices in the slice combination. Based on the strategy of reducing the number of the scanning slices in the slice combination and/or the strategy of reducing the thickness of the scanning slices in the slice combination, the medical device may reduce the number of the scanning slices and/or the thickness of the scanning slices of the slice combination in the second primary scanning condition. For example, when the slice combination in the second primary scanning condition is 16 slices*0.625 mm, the slice combination modified by the medical device may be 8 slices*0.625 mm, 16 slices*0.3125 mm, or 8 slices*0.3125 mm.

Case 4: when the event is the primary scanning condition abnormality event, the modifying strategy of the scanning condition may include a strategy of modifying the scanning dose to a preset scanning dose range. Based on the strategy of modifying the scanning dose to the preset scanning dose range, the medical device may modify the scanning dose in the second primary scanning condition to the preset scanning dose interval, for example, modifying a bulb tube current A that is not in the preset scanning dose range (greater than a maximum value of the preset scanning dose range, or smaller than a minimum value thereof) to a bulb tube current B in the preset scanning dose interval.

Case 5: when the event is the variable current abnormality event, the modifying strategy includes a strategy of reducing the scanning dose and a strategy of increasing the pitch. Based on the strategy of reducing the scanning dose, the medical device may reduce the scanning dose in the second primary scanning condition. Based on the strategy of increasing the pitch, the medical device may increase the pitch in the second primary scanning condition.

The above are non-limited examples of obtaining the auxiliary scanning condition. In some examples, an auxiliary scanning condition can be pre-configured in the medical device. In some other examples, an auxiliary scanning condition may be received from an input.

Referring back to FIG. 1, in step 102, an auxiliary scanning is performed on the object using the auxiliary scanning condition to obtain (or generate) an auxiliary image.

In step 103, a first primary scanning condition is obtained using the auxiliary scanning condition, and a primary scanning is performed on the object using the first primary scanning condition to obtain a primary image, when the primary scanning is determined to be performed based on the auxiliary image. In some implementations, a number of auxiliary images can be obtained from the auxiliary scanning in step 102, and a number of primary images can be obtained from the primary scanning in step 103. The number of the auxiliary images obtained in step 102 can be smaller than the number of the primary images obtained in step 103. The scanning dose used for the auxiliary scanning in step 102 can be less than that for the primary scanning in step 103.

In some examples, there may be one or more auxiliary images obtained during the auxiliary scanning and there may be tens or even hundreds of primary images obtained during the primary scanning, and the number of the auxiliary images can be much smaller than that of primary images. Thus, even if the auxiliary scanning is repeatedly performed on the object for multiple times, the scanning dose thereof can be much less than that of the primary scanning for one time. For at least the reasons described above, the auxiliary scanning can be added between the pilot image scanning and the primary scanning, and/or after whether the image quality of the primary image meets diagnostic requirement is predicted by analyzing the image quality of the auxiliary image obtained in the auxiliary scanning. In such a way, even if the primary scanning is finally abandoned, the final scanning dose can be much less than that of the primary scanning for one time. Otherwise, the final scanning dose for adding one or more auxiliary scanning is much less than the scanning dose for repeatedly performing the primary scanning. The reason why the primary scanning is repeatedly performed can be explained in further details in the subsequent paragraphs.

In some examples, the scanning dose for the auxiliary scanning is adjusted to be less than the scanning dose for the primary scanning, so that the scanning dose is less than that of the primary scanning for one time when the auxiliary scanning is performed on the object. For at least the reasons described above, the auxiliary scanning can be added between the pilot image scanning and the primary scanning, and/or after whether the image quality of the primary image meets diagnostic requirement is predicted by analyzing the image quality of the auxiliary image obtained in the auxiliary scanning. In such way, even if the primary scanning is finally abandoned, the final scanning dose can be much less than that of the primary scanning for one time. Otherwise, the final scanning dose for adding the auxiliary scanning is much less than the scanning dose for the primary scanning performed repeatedly.

In some examples, when the number of the auxiliary images is much smaller than that of primary images and the scanning dose for the auxiliary scanning is less than that for the primary scanning, the final scanning dose for the auxiliary scanning is less than the scanning dose for the primary scanning repeatedly performed. Even if the number of the auxiliary images is equal to or greater than the number of the primary images, the final scanning dose can also be less than the scanning dose for the primary scanning repeatedly performed as long as the scanning dose for the auxiliary scanning is less than that for the primary scanning.

After the auxiliary image is obtained, a command about whether the primary scanning is performed based on the auxiliary image can be received. The command can be obtained based on the auxiliary image. If a command to perform the primary scanning is received, the primary scanning is determined to be performed based on the auxiliary image. If a command not to perform the primary scanning is received, the auxiliary scanning condition is re-obtained and a second auxiliary scanning is performed on an object using the re-obtained auxiliary scanning condition, where subsequent processes of the auxiliary scanning are performed, which will not be repeated here.

In some examples, after the auxiliary image is obtained, if the image quality of the auxiliary image may meet the diagnostic requirement, the primary image obtained in the primary scanning may be predicted to be able to also meet the diagnostic requirement, and therefore, the primary scanning is determined to be performed based on the auxiliary image.

If the image quality of the auxiliary image cannot meet the diagnostic requirement, the primary image obtained in the primary scanning may be predicted not be able to meet the diagnostic requirement. Further, if the image quality of the auxiliary image obtained after the auxiliary scanning condition is modified, still cannot meet the diagnostic requirement, the primary scanning process may be abandoned and the primary scanning on the object is no longer performed. If the image quality of the auxiliary image obtained after the auxiliary scanning condition is modified, may meet the diagnostic requirement, the primary scanning is determined to be performed based on the auxiliary image, or the auxiliary scanning condition may be modified and then used to re-execute the processes in steps 102 and 103.

In some examples, a medical device may provide the auxiliary image to an operator. The operator can analyze the image quality of the auxiliary image, and provide the analyzed result to the medical device. The analyzed result may be as follows: 1) the image quality of the auxiliary image may meet diagnostic requirement; 2) the image quality of the auxiliary image cannot meet the diagnostic requirement, and the image quality of the auxiliary image obtained after the auxiliary scanning condition is modified, may meet the diagnostic requirement; or 3) the image quality of the auxiliary image cannot meet the diagnostic requirement, and the image quality of the auxiliary image obtained after the auxiliary scanning condition is modified, still cannot meet the diagnostic requirement.

In some examples, for the process of obtaining the first primary scanning condition using the auxiliary scanning condition, a medical device may determine that the auxiliary scanning condition is the first primary scanning condition if an operator does not modify the auxiliary scanning condition; or, the medical device may determine that the auxiliary scanning condition modified by the operator is the first primary scanning condition if the operator modifies the auxiliary scanning condition.

In some examples, the process that a medical device abandons the primary scanning may be that when analyzing that the image quality of the auxiliary image cannot meet the diagnostic requirement and the image quality of the auxiliary image obtained after the auxiliary scanning condition is modified, still cannot meet the diagnostic requirement, an operator may input a command to abandon the primary scanning process to the medical device, and the medical device abandons the primary scanning process after receiving the command. In some examples, the process that a medical device abandons the primary scanning may be that when analyzing that the image quality of the auxiliary image cannot meet the diagnostic requirement and that the auxiliary scanning condition cannot be modified, the operator may input a command to abandon the primary scanning process to the medical device, and the medical device abandons the primary scanning process after receiving the command.

The primary image can refer to a target image reconstructed in the process of image reconstruction, which can be the final image for diagnosing the object. The operator may diagnose the object based on the primary image. If the image quality of the primary image can meet diagnostic requirement, the primary image can be used to diagnose the object. If the image quality of the primary image cannot meet the diagnostic requirement, the primary image cannot be used to diagnose the object.

In some examples, a medical device may also store the obtained auxiliary image and use the auxiliary image as the primary image, and the primary image corresponding to the auxiliary image may no longer be required and the primary scanning is no longer required to be performed on an object.

In the examples of the present disclosure, the auxiliary scanning is added between the pilot image scanning and the primary scanning, and whether the image quality of the primary image meets the diagnostic requirement is predicted by analyzing the image quality of the auxiliary image obtained in the auxiliary scanning. When the diagnostic requirement is met, the primary scanning condition is determined, and the primary scanning condition is then used to perform the primary scanning on the object, to make the image quality of the primary image to meet the diagnostic requirement so as to avoid repeatedly performing the primary scanning on the object, thus the object does not need to suffer from additional scanning radiation.

Figure 3:
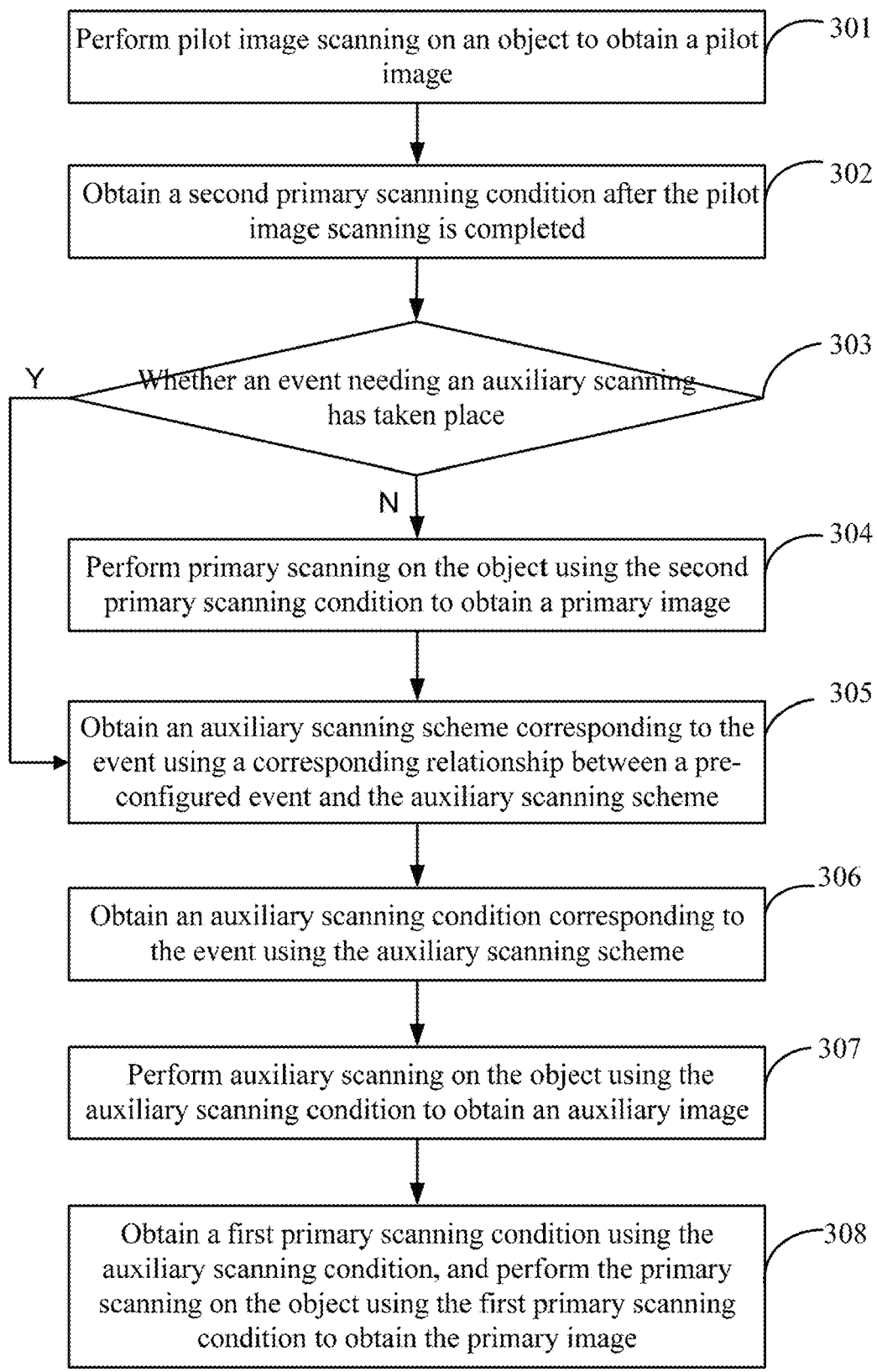
FIG. 3 is a flowchart of a process of image reconstruction in accordance with one or more another examples of the present disclosure.

The process of image reconstruction will be further described below with reference to the flowchart shown in FIG. 3.

In step 301, a pilot image scanning is performed on an object to obtain a pilot image.

In step 302, a second primary scanning condition is obtained after the pilot image scanning is completed.

In step 303, whether an event needing an auxiliary scanning has taken place is determined using at least one of the pilot image and the second primary scanning condition. If the event has not taken place, the process in step 304 is performed.

In step 304, a primary scanning is performed on the object using the second primary scanning condition to obtain a primary image.

The primary image refers to a target image reconstructed in the image reconstruction, which is the final image for diagnosing the object, and the operator may diagnose the object based on the primary image. If the image quality of the primary image meets the diagnostic requirement, the primary image may be used to diagnose the object. If the image quality of the primary image cannot meet the diagnostic requirement, the primary image cannot be used to diagnose the object.

After the second primary scanning condition is obtained, if the auxiliary scanning is not performed, the primary scanning may be performed on the object directly using the second primary scanning condition to obtain the primary image. The process is not repeated again herein.

If the event needing an auxiliary scanning has taken place is determined, the process moves to step 305. In step 305, an auxiliary scanning scheme corresponding to the event (that is, the event needing the auxiliary scanning that takes place currently) is obtained using a corresponding relationship between a pre-configured event corresponding to the event and the auxiliary scanning scheme.

In step 306, an auxiliary scanning condition corresponding to the event is obtained using the auxiliary scanning scheme.

In step 307, the auxiliary scanning is performed on the object using the auxiliary scanning condition to obtain or generate an auxiliary image.

In step 308, when a primary scanning is determined to be performed based on the auxiliary image, a first primary scanning condition is obtained using the auxiliary scanning condition, and the primary scanning is performed on the object using the first primary scanning condition to obtain or generate the primary image.

In some examples, one or more auxiliary images are obtained in the auxiliary scanning, and one or more primary images are obtained in the primary images. The number of auxiliary images can be smaller than that of primary images. The scanning dose used for the auxiliary scanning can be less than that used for the primary scanning.

The above examples will be described in detail with reference to specific application scenarios. In step 301, the medical device performs the pilot image scanning on the object to obtain the pilot image I1. In step 302, the medical device obtains the second primary scanning condition C1, which includes a scanning range F1, a bulb tube current A1, a bulb tube voltage V1, a pitch P1, a slice combination S1, a focus mode Q1, a rotational velocity S1, a scanning bed position T1 and the like. In step 304, the medical device performs the primary scanning using the second primary scanning condition C1 to obtain the primary image. In step 307 and step 308, the medical device performs the auxiliary scanning on the object using the auxiliary scanning condition to obtain the auxiliary image. When the primary scanning is determined to be performed based on the auxiliary image, the first primary scanning condition is obtained by using the auxiliary scanning condition, and the primary scanning is performed on the object using the first primary scanning condition to obtain the primary image. The processes in steps 303, 305, and 306 will be described in detail below in connection with specific application scenarios.

Application Scenario I: Metal Fixture Event

In an application scenario, an object may contain a metal fixture therein (for example, an object with bone fracture contains a metal fixture). If an operator does not notice such situation, a second primary scanning condition C1 set by the operator may be not suitable. When the medical device performs the primary scanning on the object using the second primary scanning condition C1, the image quality of the obtained primary image may not meet diagnostic requirement, which may cause to re-perform the primary scanning.

To solve the problem above, after the pilot image I1 and the second primary scanning condition C1 are obtained, in step 303, since the object contains a metal fixture, the medical device may use the pilot image I1 to determine that the object contains the metal fixture and to determine that an event needing an auxiliary scanning has taken place, and the event is a metal fixture event. In some examples, the medical device may obtain a CT value of each pixel point in the pilot image I1. If any CT value is greater than a preset first threshold, it indicates that the pixel point corresponding to the CT value is the pixel point where the metal fixture is located, so as to determine that an event needing an auxiliary scanning has taken place, and the event is the metal fixture event.

The manner in which the CT value is obtained is not repeated herein. The CT value is an attenuation value after X-ray passes through tissue of an object to be absorbed. The CT value is a measuring unit for measuring a density size of a particular local tissue or organ of an object, and can be referred to as a Hounsfield unit. For example, the CT value of the air is −1000, the CT value of the dense bone is +1000, and the CT value of the metal fixture is +1500 or more. The preset first threshold may be, for example, +1500.

In step 305, assuming that a corresponding relationship between the metal fixture event and the auxiliary scanning scheme R1 is pre-configured in the medical device, the auxiliary scanning scheme may be obtained as the auxiliary scanning scheme R1. In an example, the auxiliary scanning scheme R1 provides a modifying strategy of the scanning condition, and the modifying strategy may include a strategy of modifying the scanning range to a metal fixture range and a strategy of modifying the scanning dose to the preset scanning dose range.

In step 306, the medical device may modify a scanning range F1 to a scanning range F2 based on the strategy of modifying the scanning range to the metal fixture range. The scanning range F2 is the metal fixture range, and the metal fixture range may be a segment of area with a relatively strong metal artifact. The medical device may select the metal fixture range from the pilot image I1.

Based on the strategy of modifying the scanning dose to the preset scanning dose range, the medical device may modify the bulb tube current A1 which is not in the preset scanning dose range to the bulb tube current A2 in the preset scanning dose range and modify the bulb tube voltage V1 which is not in the preset scanning dose range to the bulb tube voltage V2 in the preset scanning dose range.

After the above process, the auxiliary scanning condition may include a scanning range F2, a bulb tube current A2, a bulb tube voltage V2, a pitch P1, a slice combination S1, a focus mode Q1, a rotational velocity S1, a scanning bed position T1, and the like.

In an example, when an object contains a metal fixture, a metal artifact is in an auxiliary image obtained by performing the auxiliary scanning on the object using an auxiliary scanning condition, which results in poorer image quality of the auxiliary image. To improve the image quality of the auxiliary image, a bulb tube current and a bulb tube voltage may be set to be larger. Based on this, the bulb tube current A2 may be larger than the bulb tube current A1, and the bulb tube voltage V2 may be larger than the bulb tube voltage V1.

In an example, after obtaining the auxiliary image and before performing the primary scanning, the medical device may also perform a process of removing metal artifact from the auxiliary image, and provide the auxiliary image after removing metal artifact and the auxiliary image before removing metal artifact to an operator. The operator then determines whether or not the processing of removing metal artifact is performed in a primary scanning process based on a comparison between the auxiliary image after removing metal artifact and the auxiliary image before removing metal artifact. If so, a medical device may also perform the processing of removing metal artifact on a primary image in the primary scanning process to improve the image quality of the primary image.

In an example, after the medical device obtains an auxiliary image, if the image quality of the auxiliary image cannot meet a diagnostic requirement, an operator may remove a metal fixture from an object and re-execute the above processes 307 and 308 to determine whether or not the image quality of the auxiliary image meets the diagnostic requirement.

Application Scenario II: Scanning Field of View Abnormality Event

In an application scenario, an object may have a large size or be located at an inappropriate position resulting in the object exceeding a scanning field of view, that is, the object is not located in a scanning centre. If an operator does not notice such a situation, based on the second primary scanning condition C1 set by the operator, the object may exceed the scanning field of view at some scanning positions, resulting in missing data at the positions, so that the image quality of a primary image cannot meet a diagnostic requirement, and especially high-density artifact may be generated at edge parts of the primary image. In this case, the operator may have to reset the second primary scanning condition C1, which may cause to re-perform the primary scanning.

To solve the problem, after obtaining the pilot image I1 and the second primary scanning condition C1, in step 303, since the scanning field of view of the object is abnormal, the medical device may use the pilot image I1 to determine that the scanning field of view of the object is abnormal and to determine that an event needing an auxiliary scanning has taken place and the event is a scanning field of view abnormality event. In an example, based on the pilot image I1, the medical device may use an image analysis technique to analyze a positional relationship between the object and a scanning bed. With the reference to FIG. 4, if the object is supposed to cover a position T1 of the scanning bed, but the object does not cover the position T1 of the scanning bed in the analysis, the scanning field of view of the object is determined to be abnormal; or, if the object is not supposed to cover a position T2 of the scanning bed, but the object has covered the position T2 of the scanning bed in the analysis, the scanning field of view of the object is determined to be abnormal.

In step 305, assuming that a corresponding relationship between the scanning field of view abnormality event and the auxiliary scanning scheme R2 is pre-configured in the medical device, an auxiliary scanning scheme may be obtained as the auxiliary scanning scheme R2. In an example, the auxiliary scanning scheme R2 provides a modifying strategy of the scanning condition, and the modifying strategy may include a strategy of modifying the scanning range to a supervision-field range and a strategy of moving a scanning bed position to a set position.

Figure 4:
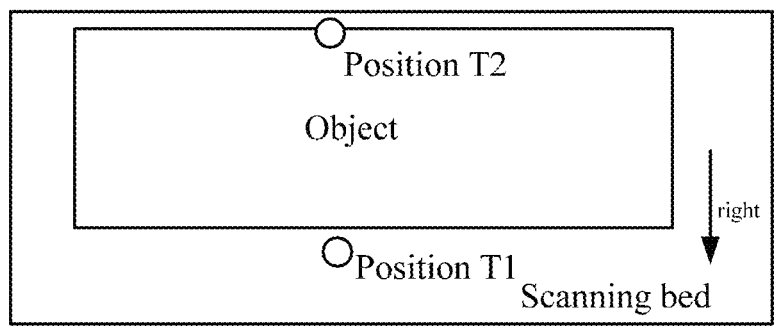
FIG. 4 is a schematic diagram of positional relationship between an object and a scanning bed in accordance with one or more examples of the present disclosure.

In step 306, the medical device may modify the scanning range F1 to a scanning range F3 based on the strategy of modifying the scanning range to the supervision-field range, where the scanning range F3 is the supervision-field range. Based on the strategy of moving the scanning bed position to the set position, the medical device may modify the scanning bed position T1 to the set position T2. As shown in FIG. 4, for example, when the object does not cover the position T1, resulting in abnormal scanning field of view of the object, the scanning bed position T1 is modified to the set position T2. For example, the scanning bed position may be moved to the right in a distance (such as 10 cm) to make the object to cover the position T1. As another example, when the object covers the position T2 resulting in abnormal scanning field of view of the object, the scanning bed position T1 is modified to the set position T2. For example, the scanning bed position may be moved to the right in a distance (such as 10 cm) to make the object to not cover the position T2.

After the above processing, the auxiliary scanning condition may include the scanning range F3, the bulb tube current A1, the bulb tube voltage V1, the pitch P1, the slice combination S1, the focus mode Q1, the rotational velocity S1, the scanning bed position T2.

Application Scenario III: Key Region Image Viewing Event

In an application scenario, an operator may need to view an image of a key region of an object (such as a lumbar intervertebral disc region). In an example, after obtaining the pilot image I1 and the second primary scanning condition C1, and when a scanning range in the second primary scanning condition C1 is a key region of the object, the medical device may use the scanning range in the second primary scanning condition C1 to determine that the key region image of the object needs to be viewed, and to determine that an event needing an auxiliary scanning has taken place and the event is a key region image viewing event.

In step 305, assuming that a corresponding relationship between the key region image viewing event and the auxiliary scanning scheme R3 is pre-configured in the medical device, an auxiliary scanning scheme may be obtained as the auxiliary scanning scheme R3. In an example, the auxiliary scanning scheme R3 provides a modifying strategy of the scanning condition, and the modifying strategy may include a strategy of reducing the number of scanning slices in a slice combination and a strategy of reducing the thickness of the scanning slices in the slice combination.

In step 306, the medical device may reduce the number of the scanning slices of the slice combination S1 and/or reduce the thickness of the scanning slices in the slice combination based on the strategy of reducing the number of scanning slices in the slice combination and/or the strategy of reducing the thickness of the scanning slices in the slice combination. For example, when the slice combination S1 is 16 slices*0.625 mm, the modified slice combination S2 may be 8 slices*0.625 mm, or 16 slices*0.3125 mm, or 8 slices*0.3125 mm, for example.

After the above processing, the auxiliary scanning condition may include the scanning range F1, the bulb tube current A1, the bulb tube voltage V1, the pitch P1, the slice combination S2, the focus mode Q1, the rotational velocity S1, the scanning bed position T1.

Since the auxiliary image from the auxiliary scanning can be utilized to predict whether the image quality of the primary image meets the diagnostic requirement, the number of the scanning slices of the slice combination S1 and/or the thickness of the scanning slices can be reduced, thus the scanning speed may be increased, so that the object receives a smaller dose of radiation.

Application Scenario IV: Primary Scanning Condition Abnormality Event

In an application scenario, a scanning dose set by an operator may not be suitable for reasons such as experience, and the image quality of the primary image obtained based on the scanning dose cannot meet a diagnostic requirement, resulting in re-performing the primary scanning. Based on this, in an example, after obtaining the pilot image I1 and the second primary scanning condition C1, and if the scanning dose in the second primary scanning condition C1 is smaller than a preset first dose, or the scanning dose is larger than a preset second dose, the medical device may determine that an event needing an auxiliary scanning has taken place and that the event is a primary scanning condition abnormality event. The preset second dose is greater than the preset first dose.

For example, a preset current range and a preset voltage range may be pre-configured in the medical device. The preset current range may be from a first bulb tube current to a second bulb tube current, and the preset voltage range may be from a first bulb tube voltage to a second bulb tube voltage. Based on this, when the bulb tube current A1 is smaller than the first bulb tube current, or greater than the second bulb tube current, it is determined that an event needing an auxiliary scanning has taken place and the event is a primary scanning condition abnormality event. And/or, when the bulb tube voltage V1 is smaller than the first bulb tube voltage, or greater than the second bulb tube voltage, it is determined that an event requiring an auxiliary scanning has taken place and the event is a primary scanning condition abnormality event.

In step 305, assuming that a corresponding relationship between the primary scanning condition abnormality event and the auxiliary scanning scheme R4 is pre-configured in the medical device, an auxiliary scanning scheme may be obtained as the auxiliary scanning scheme R4. In an example, the auxiliary scanning scheme R4 provides a modifying strategy of the scanning condition, and the modifying strategy may include a strategy of modifying the scanning dose to a preset scanning dose range. For example, the strategy of modifying a bulb tube current to a preset current range and/or a strategy of modifying a bulb tube voltage to a preset voltage range may be included.

In step 306, based on the strategy of modifying the scanning dose to the preset scanning dose range, the medical device may modify the bulb tube current A1 that is not in the preset current range to the bulb tube current A2 in the preset current range, and may modify the bulb tube voltage V1 which is not in the preset voltage range to the bulb tube voltage V2 in the preset voltage range.

After the above processing, the auxiliary scanning condition may include the scanning range F1, the bulb tube current A2, the bulb tube voltage V2, the pitch P1, the slice combination S1, the focus mode Q1, the rotational velocity S1, the scanning bed position T1.

Application Scenario V. Variable Current Abnormality Event

In an application scenario, to reduce the radiation on an object, a variable current technology may be used to perform a primary scanning on the object. In the variable current technology, since X-ray of a same intensity has different attenuation paths through the object at different scanning angles, attenuation values through the object are different. Therefore, according to differences between the attenuation values, different bulb tube currents may be used at different scanning angles. A stronger bulb tube current is used at the scanning angle with a greater attenuation value, and a weaker bulb tube current is used at the scanning angle with a smaller attenuation value. Based on the variable current technology, the medical device may use a current curve to perform the primary scanning on the object. The current curve is expressed as a corresponding relationship between the scanning angles and the bulb tube currents. In the primary scanning process, for each scanning angle, the bulb tube current corresponding to the scanning angle may be obtained from the current curve and the primary scanning is performed at the scanning angle based on the bulb tube current.

Figure 5:
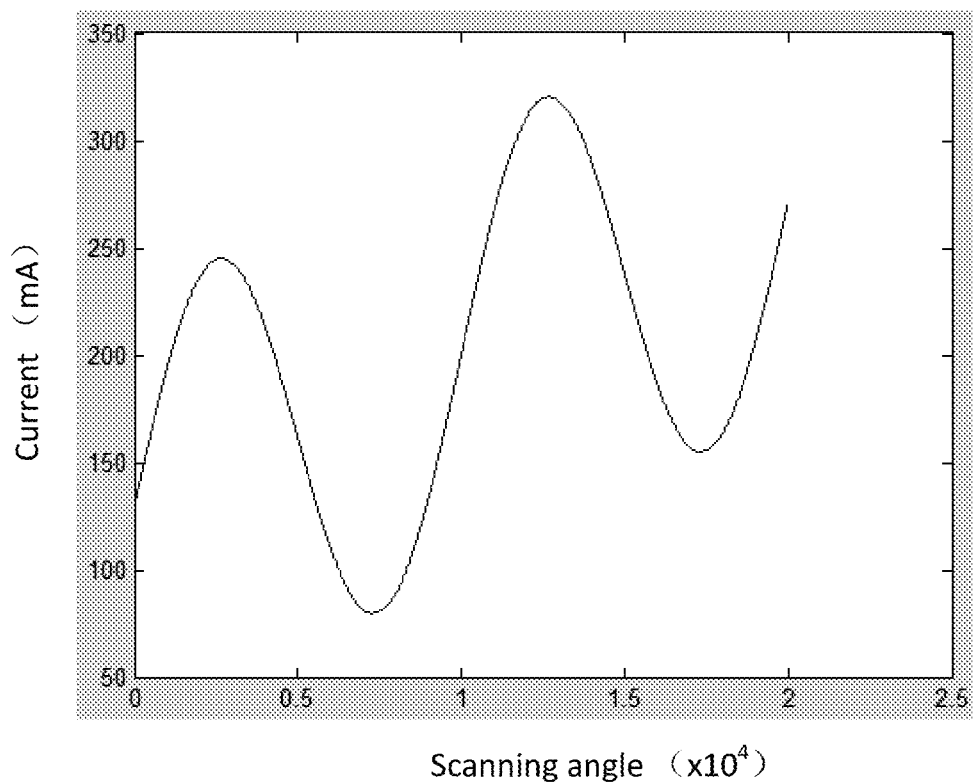
FIG. 5 is a graph showing a relationship between currents and scanning angles in accordance with one or more examples of the present disclosure.

FIG. 5 is a graph of an example current curve. At the scanning angle 0, the bulb tube current may be 140 mA, and the primary scanning can be performed using 140 mA of the bulb tube current. At the scanning angle 2000, the bulb tube current may be 220 mA, and the primary scanning can be performed using 220 mA of the bulb tube current, and the like. Herein, a unit of the scanning angle is degree. In FIG. 5, 360 degrees are divided into 5000 parts, each of which is a scanning angle. Therefore, the above scanning angle 0 indicates 0*(360/5000) degrees, that is, 0 degree. The scanning angle 2000 indicates 2000*(360/5000) degrees, that is, 144 degrees. Other scanning angles are similar to this.

In practical applications, the bulb tube current corresponding to each of the scanning angles in the current curve is calculated by the attenuation path by which the X-ray passes through the object, but the real attenuation path is an unknown value before the scanning is completed, and may only be estimated in a particular way. The specific algorithm will not be repeated. For example, before the primary scanning is performed at the scanning angle 2000, the attenuation path by which the X-ray passes through the object may only be estimated in a particular way at the scanning angle 2000, and the bulb tube current at the scanning angle 2000 is calculated based on the attenuation path. For example, the bulb tube current is 220 mA in FIG. 5. Further, since there are some errors in the algorithm for estimating the attenuation path, there may be an error in the estimated attenuation path, and there may be an error in the bulb tube current calculated based on the attenuation path, resulting in inaccurate bulb tube current value corresponding to each angle in the current curve, so that when the medical device performs the primary scanning on the object using the current curve, the image quality of the obtained primary image may not meet the diagnostic requirement, resulting in re-performing the primary scanning.

Figure 6:
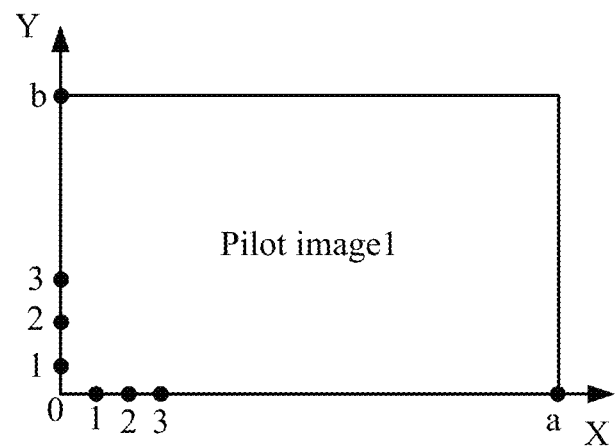
FIG. 6 is a schematic diagram of a pilot image in accordance with one or more examples of the present disclosure.

To solve the problem, in some implementations, after obtaining the pilot image I1 and the second primary scanning condition C1, the medical device may use the pilot image I1 to predict whether the current curve is abnormal, and to determine whether an event needing an auxiliary scanning has taken place and the event is a variable current abnormality event. In some examples, for the process that the medical device uses the pilot image I1 to predict determine whether the current curve is abnormal, as shown in FIG. 6, the horizontal direction of the pilot image I1 may be referred to as X direction and the vertical direction of the pilot image I1 may be referred to as Y direction. Assuming that the pilot image I1 includes a*b pixel points, the number of pixel points in the X direction is a, and the number of pixel points in the Y direction is b. The CT value corresponding to each pixel point in the Y direction may be calculated, which is a sum of the CT values of the pixel points in the X direction corresponding to the pixel point in the Y direction. In addition, b pixel points in the Y direction are divided into multiple groups, each of which contains adjacent N pixel points. The CT values corresponding to the N pixel points of each group are averaged to obtain the group CT value corresponding to the group, and a difference between the group CT values of two adjacent groups is compared. When the difference is greater than a preset threshold, that the current curve is abnormal is predicted. When all the differences are not greater than the preset threshold, that current curve is not abnormal is predicted.

Assuming that b is 9 and N is 3, the group 1 includes a pixel point 1, a pixel point 2, and a pixel point 3, the group 2 includes a pixel point 4, a pixel point 5, and a pixel point 6, and the group 3 includes a pixel point 7, a pixel point 8, and a pixel point 9. The CT values corresponding to the pixel point 1, the pixel point 2 and the pixel point 3 of the group 1 are averaged to obtain a group CT value of the group 1. The CT values corresponding to the pixel point 4, the pixel point 5, and the pixel point 6 of the group 2 are averaged to obtain a group CT value of the group 2. And the CT values corresponding to the pixel point 7, the pixel point 8, and the pixel point 9 of the group 3 are averaged to obtain a group CT value of the group 3. A difference 1 between the group CT value of the group 1 and the group CT value of the group 2 is calculated and the difference 2 between the group CT value of the group 2 and the group CT value of the group 3 is calculated. If the difference 1 and/or the difference 2 are greater than the preset threshold, that the current curve is abnormal is predicted; and if the difference 1 and the difference 2 are not greater than the preset threshold, that the current curve is not abnormal is predicted.

In an example, after obtaining the pilot image I1, the medical device may estimate the attenuation path using the pilot image I1. Then the bulb tube current is calculated based on the attenuation path to obtain the current curve. When the difference between the CT values of two adjacent groups is greater than the preset threshold, it indicates that the attenuation value of the pilot image I1 in the Y direction is greatly fluctuated. In this case, there is a large error in the attenuation path estimated by the pilot image I1. Therefore, there is also a large error in the bulb tube current calculated based on the attenuation path, so that the bulb tube current in the current curve is not accurate. Based on this, when the difference between the group CT values of two adjacent groups is greater than the preset threshold, the medical device may predict that the current curve is abnormal.

Referring back to FIG. 3, in step 305, assuming that a corresponding relationship between the variable current abnormality event and the auxiliary scanning scheme R5 is pre-configured on the medical device, an auxiliary scanning scheme may be obtained as the auxiliary scanning scheme R5. In an example, the auxiliary scanning scheme R5 provides a modifying strategy of the scanning condition which may include, but is not limited to, a strategy of reducing a scanning dose and a strategy of increasing a pitch.

In step 306, based on the strategy of reducing the scanning dose, the bulb tube current A1 and/or the bulb tube voltage V1 may be reduced. For example, the bulb tube current A1 is reduced to the bulb tube current A2, and/or the bulb tube voltage V1 is reduced to the bulb tube voltage V2. Based on the strategy of increasing the pitch, the pitch may be increased. For example, the pitch P1 is increased to the pitch P2.

After the above processing, the auxiliary scanning condition may include the scanning range F1, the bulb tube current A2, the bulb tube voltage V2, the pitch P2, the slice combination S1, the focus mode Q1, the rotational velocity S1, the scanning bed position T1.

In an example, a reduced amount between the bulb tube current A1 and the bulb tube current A2 may be chosen according to actual experience to ensure that the bulb tube current A2 is less than the bulb tube current A1. For example, the bulb tube current A1 may be 300 mA, while the bulb tube current A2 may be 30 mA. A reduced amount between the bulb tube voltage V1 and the bulb tube voltage V2 may be chosen according to actual experience to ensure that the bulb tube voltage V2 is less than the bulb tube voltage V1. For example, the bulb tube voltage may be chosen from several fixed values, such as 120 kV, 80 kV, 60 kV, 40 kV, etc. When the bulb tube voltage V1 is 120 kV, the bulb tube voltage V2 may be 80 kV, 60 kV and the like. In addition, an increased amount between the pitch P1 and the pitch P2 may be chosen according to actual experience to ensure that the pitch P2 is greater than the pitch P1. For example, the pitch P2 is twice or three times the pitch P1, or the pitch P2 is a maximum pitch, and the like.

In an auxiliary scanning process, the radiation to an object can be reduced by reducing a scanning dose. A scanning speed may be increased by increasing a pitch. For example, the maximum pitch is used to maximize the scanning speed.

In an example, in an auxiliary scanning process, an accurate attenuation path at each scanning angle may also be obtained, and a more accurate current curve can be calculated based on the accurate attenuation path to use the more accurate current curve to perform a primary scanning in a primary scanning process. When the primary scanning is performed using the more accurate current curve, the scanning dose may be reduced to reduce the radiation to the object.

For convenience of description, the above current curve obtained based on the pilot image I1 is referred to as the current curve 1, and the more accurate current curve obtained in the auxiliary scanning process is referred to as the current curve 2.

In an example, to illustrate a process of calculating the current curve 2 using the accurate attenuation path, relationships between a scanning position, an auxiliary image, a primary image, and a scanning angle are first introduced.

After an object is placed on a scanning bed, the scanning bed is moved to a particular position, and then scanning is performed for a period of time. The particular position is a scanning position. After the scanning is completed, the scanning bed may be moved to a next position and scanning is performed again for a period of time, and the next position is a new scanning position. After the scanning is completed, the scanning bed may be moved to another next position again, and the like. Each position that the scanning bed moved to is a scanning position, where scanning is performed for a period of time.

In the process of scanning for a period of time for each scanning position, in a non-limited example, when an X-ray generator is rotated by 360 degrees around an object, an auxiliary image/a primary image is obtained, and the 360 degrees are divided into 5000 parts (as shown in the graph of the current curve in FIG. 5), each of which is a scanning angle. In FIG. 5, the scanning angles 0-5000 are all the scanning angles corresponding to one scanning position, the scanning angles 5001-10000 are all the scanning angles corresponding to another scanning position, the scanning angles 10001-15000 are all the scanning angles corresponding to still another scanning position, and the like.

For each scanning position, the object is scanned at 5000 scanning angles. The auxiliary image/the primary image may be obtained based on scanning results obtained at 5000 scanning angles. After the above processing is performed at each scanning position, multiple auxiliary images/primary images may be obtained.

Further, in a non-limited example, the auxiliary image of the scanning position 1 and the primary images of the scanning position 1, the scanning position 2, the scanning position 3, the scanning position 4, and the scanning position 5 are needed to be obtained respectively. In the auxiliary scanning process, at the scanning position 1, the object is scanned at 5000 scanning angles of 0-5000 to obtain the auxiliary image of the scanning position 1, and the attenuation path by which the X-ray passes through the object at the 5000 scanning angles may be counted. Therefore, the bulb tube current corresponding to each scanning angle may be calculated using the attenuation path at each of the 5000 scanning angles to obtain the current curve 2 of the scanning position 1. Accordingly, the current curve 2 calculated based on the true attenuation path is more accurate than the current curve 1.

In the primary scanning process, at the scanning position 1, the primary scanning may be performed using the current curve 2 instead of the current curve 1. In addition, for other scanning positions (such as the scanning position 2, the scanning position 3, the scanning position 4, and the scanning position 5), the attenuation paths of other scanning positions may be estimated using each attenuation path corresponding to the current curve 2 of the scanning position 1. Since each attenuation path corresponding to the current curve 2 of the scanning position 1 is true attenuation path, the estimated attenuation paths of other scanning positions are more accurate and the current curve calculated using these attenuation paths is more accurate.

For the primary scanning process, when the primary scanning is performed using the current curve 1, the scanning dose used at the scanning position 1 is assumed to be 300 milliampere seconds, the scanning dose used at the scanning position 2 is assumed to be 200 milliampere seconds, the scanning dose used at the scanning position 3 is assumed to be 300 milliampere seconds, the scanning dose used at the scanning position 4 is assumed to be 400 milliampere seconds, and the scanning dose used at the scanning position 5 is assumed to be 300 milliampere seconds. When the current curve 1 is used, a total of the scanning doses is 1500 milliampere seconds. The scanning dose is the bulb tube current used at 5,000 scanning angles multiplied by a sum of time at 5,000 scanning angles. For example, assuming that 5000 scanning angles are passed per second, the time at one scanning angle is 1/5000. At the first scanning angle, the bulb tube current is multiplied by the time, which is equivalent to 140 milliamps multiplied by 1/5000 seconds, and the like. The bulb tube current used at 5,000 scanning angles multiplied by the sum of time is obtained, that is, the scanning dose. When the primary scanning is performed using the current curve 2, the scanning dose used at the scanning position 1 is assumed to be 300 milliampere seconds, the scanning dose used at the scanning position 2 is assumed to be 100 milliampere seconds, the scanning dose used at the scanning position 3 is assumed to be 200 milliampere seconds, the scanning dose used at the scanning position 4 is assumed to be 300 milliampere seconds, and the scanning dose used at the scanning position 5 is assumed to be 300 milliampere seconds. When the current curve 2 is used, a total of the scanning doses is 1200 milliampere seconds, which is less than the total of the scanning doses when using the current curve 1. Obviously, when the primary scanning is performed using the current curve 2, the scanning dose may be reduced to reduce the radiation to the object.

A device of image reconstruction and a medical device are also provided in accordance with one or more examples of the present disclosure correspondingly to the examples of the method of image reconstruction.

A hardware structure diagram of a medical device in accordance with one or more examples of the present disclosure is shown in FIG. 2. The hardware structure of the medical device has been described above, and is not repeated here. In an example, a non-transitory computer-readable storage medium having instructions stored thereon, when executed by one or more processors 2115, causes the one or more processors 2115 to perform a method of image reconstruction. The method includes acquiring an auxiliary scanning condition, performing auxiliary scanning on an object using the auxiliary scanning condition to obtain an auxiliary image, and obtaining a first primary scanning condition using the auxiliary scanning condition and performing primary scanning on the object using the first primary scanning condition to obtain a primary image, when the primary scanning is determined to be performed based on the auxiliary image. The computer-readable storage medium may include the storage 2116 in FIG. 2. A system of image reconstruction includes the one or more processors and the computer-readable storage medium.

It is noted that the medical device in FIG. 2 is only an example of the present disclosure, but in other examples, the medical device may further include other elements not shown in FIG. 2.

Figure 7:
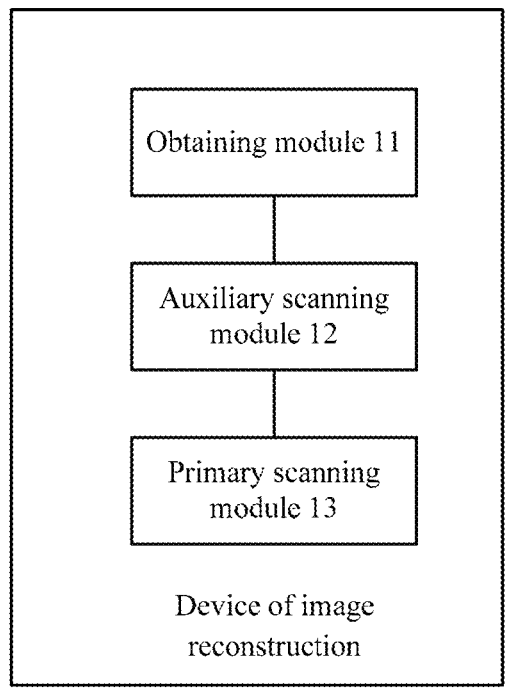
FIG. 7 is a structure diagram of a device of image reconstruction in accordance with one or more examples of the present disclosure.

FIG. 7 is a block diagram of a device of image reconstruction in accordance with one or more examples of the present disclosure. The device includes an obtaining module 11, an auxiliary scanning module 12, and a primary scanning module 13.

The acquiring module 11 is configured to acquire an auxiliary scanning condition. The auxiliary scanning module 12 is configured to perform auxiliary scanning on an object using the auxiliary scanning condition to obtain an auxiliary image. The primary scanning module 13 is configured to obtain a first primary scanning condition using the auxiliary scanning condition, and perform primary scanning on the object using the first primary scanning condition to obtain a primary image, when the primary scanning is determined to be performed based on the auxiliary image.

A number of the auxiliary images obtained by the auxiliary scanning module 12 is less than that of the primary images obtained by the primary scanning module 13, and/or the scanning dose used for the auxiliary scanning by the auxiliary scanning module 12 is less than that used for the primary scanning by the primary scanning module 13.

In an example, the obtaining module 11 includes a determining sub-module, a first obtaining sub-module, and a second obtaining sub-module. The determining sub-module is configured to determine whether an event needing an auxiliary scanning has taken place. The first obtaining sub-module is configured to obtain an auxiliary scanning scheme corresponding to the event using a corresponding relationship between a pre-configured event and an auxiliary scanning scheme if a determining result is yes. The second obtaining sub-module is configured to obtain the auxiliary scanning condition corresponding to the event using the auxiliary scanning scheme.

The determining sub-module is specifically configured to perform pilot image scanning on the object to obtain a pilot image and obtain a second primary scanning condition in the process of determining whether an event needing an auxiliary scanning has taken place, and determine whether an event needing an auxiliary scanning has taken place, using at least one of the pilot image and the second primary scanning condition The determining sub-module 111 is specifically configured to determine that an event needing an auxiliary scanning has taken place and the event is a metal fixture event when that the object contains a metal fixture is determined using the pilot image; or determine that an event needing an auxiliary scanning has taken place and the event is a scanning field of view abnormality event when that the scanning field of view of the object is abnormal is determined using the pilot image; or determine that an event needing an auxiliary scanning has taken place and the event is a key region image viewing event when that the key region image of the object needs to be viewed is determined using the second primary scanning condition; or determine that an event needing an auxiliary scanning has taken place and the event is a primary scanning condition abnormality event when the scanning dose included in the second primary scanning condition is less than a preset first dose or the scanning dose is greater than a preset second dose which is greater than the preset first dose; or determine that an event needing an auxiliary scanning has taken place and the event is a variable current abnormality event when that a current curve is abnormal is predicted using the pilot image. The current curve is expressed as a corresponding relationship between a scanning angle and a bulb tube current, and in the primary scanning process, the bulb tube current corresponding to each scanning angle is obtained from the current curve for the scanning angle, and the primary scanning is performed at the scanning angle based on the bulb tube current.

In an example, the second obtaining sub-module is specifically configured to analyze a modifying strategy of the scanning condition from the auxiliary scanning scheme, and modify the second primary scanning condition using the modifying strategy to obtain the auxiliary scanning condition corresponding to the event in the process of acquiring the auxiliary scanning condition corresponding to the event using the auxiliary scanning scheme.

In an example, each of the first primary scanning condition and the second primary scanning condition include one or more of a scanning range, a scanning dose, a pitch, a slice combination, a focus mode, a rotational velocity, a scanning bed position, and any combination thereof. The scanning dose includes at least one of a bulb tube current and a bulb tube voltage. The slice combination includes a number of scanning slices and a thickness of the scanning slices. The modifying strategy includes a strategy of modifying the scanning range to a metal fixture range and a strategy of modifying the scanning dose to a preset scanning dose range, when the event is a metal fixture event; or the modifying strategy includes a strategy of modifying the scanning range to a supervision-field range and a strategy of moving the scanning bed position to a set position, when the event is a scanning field of view abnormality event; or the modifying strategy includes at least one of a strategy of reducing the number of scanning slices in the slice combination and/or a strategy of reducing the thickness of the scanning slices in the slice combination when the event is a key region image viewing event; or the modifying strategy includes a strategy of modifying the scanning dose to a preset scanning dose range when the event is a primary scanning condition abnormality event; or the modifying strategy includes a strategy of reducing the scanning dose and a strategy of increasing the pitch when the event is a variable current abnormality event.

The primary scanning module 13 is further configured to receive a command obtained based on the auxiliary image about whether or not the primary scanning is performed, and determine based on the auxiliary image that the primary scanning is performed if a command to perform the primary scanning is received.

The auxiliary scanning module 12 is further configured to receive a command obtained based on the auxiliary image about whether or not the primary scanning is performed, and re-obtain the auxiliary scanning condition and execute the process of performing the auxiliary scanning on the object with the auxiliary scanning condition, using the re-obtained auxiliary scanning condition if a command to not perform the primary scanning is received.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

The foregoing descriptions are merely preferred examples of the present application and not intended to limit the present application. Any modification, equivalent replacement, improvement and the like made within the spirit and principles of the present application should fall into the scope of protection of the present application.

The invention claimed is:

1. A method of image reconstruction, comprising:
performing a pilot image scanning to generate a pilot image;
determining a first primary scanning condition;
determining an event indicating a need for an auxiliary scanning occurs using at least one of the pilot image or the first primary scanning condition;
obtaining an auxiliary scanning condition according to the event;
performing the auxiliary scanning on an object using the auxiliary scanning condition to generate an auxiliary image; and
in response to a determination to perform a primary scanning based on the auxiliary image, determining a second primary scanning condition based on the auxiliary scanning condition and performing the primary scanning on the object using the second primary scanning condition to generate a primary image.

2. The method of claim 1, wherein performing the auxiliary scanning comprises generating a plurality of auxiliary images,
wherein performing a primary scanning comprises generating a plurality of primary images, and
wherein a number of the plurality of auxiliary images is smaller than a number of the plurality of the primary images.

3. The method of claim 1, wherein a scanning dose for the auxiliary scanning is smaller than a scanning dose for the primary scanning.

4. The method of claim 1, wherein obtaining an auxiliary scanning condition comprises:
determining an auxiliary scanning scheme corresponding to the event based on a pre-configured relationship between the event and the auxiliary scanning scheme; and
obtaining the auxiliary scanning condition corresponding to the event using the auxiliary scanning scheme.

5. The method of claim 1, wherein determining an event indicating a need for an auxiliary scanning occurs comprises at least one of:
determining that the object contains a metal fixture using the pilot image and the event is a metal fixture event,
determining that a scanning field of view of the object is abnormal using the pilot image and the event is a scanning field of view abnormality event,
determining that a key region image of the object needs to be viewed using the first primary scanning condition and the event is a key region image viewing event,
determining that a scanning dose in the first primary scanning condition is less than a preset first dose or greater than a preset second dose and the event is a primary scanning condition abnormality event, the preset second dose being greater than the preset first dose, or
determining that a current curve is predicted by using the pilot image to be abnormal and the event is a variable current abnormality event, wherein the current curve indicates a relationship between scanning angles and bulb tube currents, and the primary scanning is performed at each of the scanning angles based on a corresponding bulb tube current that is determined based on the current curve.

6. The method of claim 5, wherein determining that a current curve is predicted by using the pilot image to be abnormal comprises:
determining, based on the pilot image, that a difference between attenuation values of adjacent groups of pixel points is greater than a preset threshold,
wherein each of the adjacent groups includes a plurality of adjacent pixel points along a first direction of the pilot image, and an attenuation value of each pixel point along the first direction is a sum of attenuation values of corresponding pixel points along a second direction of the pilot image perpendicular to the first direction, and the attenuation values are associated with the bulb tube currents and the scanning angles.

7. The method of claim 4, wherein obtaining the auxiliary scanning condition corresponding to the event using the auxiliary scanning scheme comprises:
analyzing a modifying strategy from the auxiliary scanning scheme; and
modifying the first primary scanning condition using the modifying strategy to obtain the auxiliary scanning condition corresponding to the event.

8. The method of claim 7, wherein the first primary scanning condition comprises one or more of a scanning range, a scanning dose, a pitch, a slice combination, a focus mode, a rotational velocity, and a scanning bed position, and
wherein the scanning dose comprises at least one of a bulb tube current and a bulb tube voltage, and the slice combination comprises a number of scanning slices and a thickness of the scanning slices.

9. The method of claim 8, wherein the modifying strategy comprises at least one of:
a strategy of modifying the scanning range to a metal fixture range and a strategy of modifying the scanning dose to a preset scanning dose range, when the event is a metal fixture event,
a strategy of modifying the scanning range to a supervision-field range and a strategy of moving the scanning bed position to a set position, when the event is a scanning field of view abnormality event, at least one of a strategy of reducing the number of scanning slices in the slice combination and a strategy of reducing the thickness of the scanning slices in the slice combination, when the event is a key region image viewing event,
a strategy of modifying the scanning dose to a preset scanning dose range, when the event is a primary scanning condition abnormality event, or
a strategy of reducing the scanning dose and a strategy of increasing the pitch, when the event is the variable current abnormality event.

10. The method of claim 1, wherein the determination to perform the primary scanning based on the auxiliary image comprises one of:
a determination that an image quality of the auxiliary image meets a diagnostic requirement for the object, or
a determination that an image quality of the auxiliary image cannot meet the diagnostic requirement and that an image quality of a second auxiliary image with a modified auxiliary scanning condition meets the diagnostic requirement.

11. The method of claim 1, further comprising:
providing the auxiliary image to an operator;
receiving an analyzed result of the auxiliary image from the operator; and
determining to perform the primary scanning based on the received analyzed result by determining one of:
the image quality of the auxiliary image meets a diagnostic requirement for the object, and
the image quality of the auxiliary image does not meet the diagnostic requirement, and an image quality of a second auxiliary image with a modified auxiliary scanning meets the diagnostic requirement.

12. The method of claim 1, further comprising one of:
in response to receiving a command to perform the primary scanning, determining to perform the primary scanning based on the auxiliary image, and
in response to receiving a command not to perform the primary scanning, re-obtaining the auxiliary scanning condition based on the auxiliary image and performing a second auxiliary scanning using the re-obtained auxiliary scanning condition.

13. The method of claim 1, wherein determining a second primary scanning condition based on the auxiliary scanning condition comprises:
analyzing the auxiliary image based on a diagnostics requirement; and
modifying, based on a result of the analyzing, the auxiliary scanning condition to be the second primary scanning condition.

14. The method of claim 1, wherein determining a second primary scanning condition based on the auxiliary scanning condition comprises:
determining that the auxiliary scanning condition is not modified by an operator; and
determining the auxiliary scanning condition to be the second primary scanning condition.

15. The method of claim 1, wherein determining a second primary scanning condition based on the auxiliary scanning condition comprises:
determining that the auxiliary scanning condition is modified by an operator; and
determining the modified auxiliary scanning condition to be the second primary scanning condition.

16. The method of claim 1, further comprising:
determining, based on the auxiliary image generated at a first scanning position, first attenuation paths at a plurality of respective scanning angles, each of the first attenuation paths corresponding to a respective bulb tube current;
generating a first current curve to indicate a relationship between the respective scanning angles and the respective bulb tube currents; and
performing the primary scanning at the first scanning position using the determined first current curve.

17. The method of claim 1, further comprising:
estimating a second attenuation path at each of the plurality of scanning angles at a second scanning position using a first attenuation path of the first current curve corresponding to the scanning angle;
determining a second current curve based on the estimated second attenuation paths; and
performing a second primary scanning at the second scanning position using the determined second current curve.

18. A system for image reconstruction, comprising:
one or more processors; and
a non-transitory computer-readable storage medium having instructions stored thereon which, when executed by the one or more processors, cause the one or more processors to perform a method of image reconstruction, the method comprising:
performing a pilot image scanning to generate a pilot image;
determining a first primary scanning condition;
determining an event indicating a need for an auxiliary scanning occurs by using at least one of the pilot image or the first primary scanning condition;
obtaining an auxiliary scanning condition according to the event;
performing the auxiliary scanning on an object using the auxiliary scanning condition to generate an auxiliary image; and
in response to a determination to perform a primary scanning based on the auxiliary image, determining a second primary scanning condition based on the auxiliary scanning condition and performing the primary scanning on the object using the second primary scanning condition to generate a primary image.

19. A non-transitory computer-readable storage medium having instructions stored thereon which, when executed by one or more processors, cause the one or more processors to perform a method of image reconstruction, the method comprising:
performing a pilot image scanning to generate a pilot image;
determining a first primary scanning condition;
determining an event indicating a need for an auxiliary scanning occurs by using at least one of the pilot image or the first primary scanning condition;
obtaining an auxiliary scanning condition according to the event;
performing the auxiliary scanning on an object using the auxiliary scanning condition to generate an auxiliary image; and
in response to a determination to perform a primary scanning based on the auxiliary image, determining a second primary scanning condition based on the auxiliary scanning condition and performing the primary scanning on the object using the second primary scanning condition to generate a primary image.

* * * * *